United States Patent [19]

Stephan

[11] 4,318,902

[45] Mar. 9, 1982

[54] CONCENTRATED IMMUNOGLOBULIN SOLUTION SUITED FOR INTRAVENOUS ADMINISTRATION

[75] Inventor: Wolfgang Stephan, Dreieich, Fed. Rep. of Germany

[73] Assignee: Biotest-Serum-Institut GmbH, Frankfurt, Fed. Rep. of Germany

[21] Appl. No.: 110,038

[22] Filed: Jan. 7, 1980

[30] Foreign Application Priority Data

Jan. 18, 1979 [DE] Fed. Rep. of Germany ....... 2901882

[51] Int. Cl.³ ............................................ A61K 39/395
[52] U.S. Cl. ...................................... 424/85; 424/87; 260/112 B
[58] Field of Search ................ 260/112 B; 424/85, 86, 424/87, 101, 177

[56] References Cited

U.S. PATENT DOCUMENTS 3,597,409  8/1971  Breuer ............................ 260/112 B

FOREIGN PATENT DOCUMENTS 1370553  7/1964  France .
872122  7/1961  United Kingdom .
1244245  8/1971  United Kingdom .

OTHER PUBLICATIONS

Chemical Abstracts, vol. 71, No. 11, 1969, p. 187, Abstract No. 47731v, Stephan, W., "Elimination of Complement Fixation in γ-Globulin by Chemical Modification with β-Propiolactone".

Van Der Hoven, A., et al., Immunochemistry, vol. 10, pp. 107–114, 1973.

Chemical Abstracts, vol. 78, No. 17, Apr. 30, 1973, Abstract No. 109110x, p. 314, A. Van Der Hoven et al.; "Isolation of Immunogenically Pure IgM from Cohn Fraction III of Pools Normal Human Plasma".

*Primary Examiner*—Blondel Hazel
*Attorney, Agent, or Firm*—Sprung, Felfe, Horn, Lynch & Kramer

[57] ABSTRACT

A process for the preparation of an immunoglobulin solution containing IgM in concentrated form and suited for intravenous administration, comprising treating an IgM-containing protein fraction obtained by conventional fractionation from blood plasma or serum with β-propiolactone in an amount such that the ratio of β-propiolactone to a 5% solution of the IgM-containing proteins is from about 0.05 to 0.15 ml per 100 ml. Advantageously, prior to the treatment with β-propiolactone the IgM-containing protein fraction is freed of lipids by treatment with colloidal silica gel and with crosslinked dextrans or diethylaminoethyl cellulose. The starting material used is a Cohn fraction III of human blood plasma which has been dissolved in physiological saline solution to a concentration of about 5% protein, the treatment with β-propiolactone is carried out at about 20° to 37° C. for about 4 to 6 hours until a substantially constant pH of about 8 is obtained, and the solution is thereafter sterile filtered.

10 Claims, No Drawings

CONCENTRATED IMMUNOGLOBULIN SOLUTION SUITED FOR INTRAVENOUS ADMINISTRATION

BACKGROUND OF THE INVENTION

The invention relates to a process for the preparation of an immunoglobulin solution suited for intravenous administration and containing IgM in somewhat concentrated form, wherein an IgM-containing protein fraction obtained by a conventional fractionating process from blood plasma or serum is treated with such amounts of β-propiolactone that the ratio of β-propiolactone to a 5% solution of the IgM-containing proteins is from about 0.05 to 0.15 ml per 100 ml, and is then worked up in known manner.

The IgM-containing immunoglobulin preparation prepared in accordance with the invention and suited for intravenous administration has a high antibody activity against gram-negative and gram-positive bacteria.

While a number of processes for the preparation of intravenously compatible immunoglobulin preparations of the IgG type and containing primarily antibodies against viruses has been developed, such as degradation by means of pepsin (Schultze, H. E., and G. Schwick, Dtsch. med. Wochenschrift 87, 1643 [1962]), degradation by means of plasmin (Barandun, S., et. al., Vox Sang. 28, 157 [1975]), degradation by means of hydrochloric acid (Barandun, S., et. al., Vox Sang. 7, 187 [1962]), or chemical modification by means of β-propiolactone (Stephan, W., Z. Klin. Chem. Klin. Biochem. 7, 282 [1969]), there is as yet no method that would permit the preparation of intravenously compatible, highly purified immunoglobulin preparations containing IgM in the concentrated form required for the control of bacterial infections, although IgM-containing fractions, such as Cohn Fraction III, have been available since the years 1940 to 1950 when alcohol-fractionation techniques were developed. The fact that nonetheless no intravenously compatible IgM concentrates have been made available up to now is probably attributable to the structural differences between the IgM and IgG molecules with respect to the interrelation between anticomplementary activity and intravenous incompatibility.

In the light of the present state of the art, a denaturation due to the fractionating process induces at the Fc site of the antibody molecule a so-called anticomplementary activity, which is responsible for the intravenous incompatibility of fractionated immunoglobulins that have been not been subjected to a special treatment. Since the IgM antibody contains five Fc sites per molecule, in contrast to the IgG antibody which only contains one Fc site per molecule, it was to be expected that the anticomplementary activity of IgM-containing immunoglobulin preparations could be overcome only through a drastic increase in the concentration of the modifiers (enzymes and acylating agents), which, however, would result in a substantial loss of antibody activity, as has been shown by the example of chemical modification of IgG.

SUMMARY OF THE INVENTION

Surprisingly, it has now been found that despite a buildup of the anticomplementarily active Fc sites of the IgM molecule its anticomplementary activity can be overcome with amounts of β-propiolactone as small as those used in the preparation of intravenously compatible immunoglobulin of the IgG type in accordance with German patent application DAS No. 17 92 555, namely, about 0.05 to 0.15 ml of β-propiolactone per 100 ml of a 5% immunoglobulin solution.

By the process of the invention, it thus becomes possible to render immunoglobulin solutions containing IgM in concentrated form intravenously compatible while largely preserving their antibody activities.

The intravenously compatible immunoglobulin solution containing IgM in concentrated form is free of anticomplementary activity and possesses high antibody activity against bacterial pathogens.

In the practice of the process in accordance with the invention, an IgM-containing protein fraction obtained by one of the conventional fractionating processes from blood plasma or serum is treated with such amounts of β-propiolactone that the ratio of β-propiolactone to a 5% solution of the IgM-containing proteins is from 0.05 to 0.15 ml per 100 ml. IgM-containing fractions from Cohn's alcohol fractionation of human blood plasma, for example, or from the Rivanol (6,9-diamino-2-ethoxyacridine)/ammonium sulfate fractionation may be used as starting materials. A particularly preferred starting material is Cohn Fraction III from human plasma. Such an IgM-containing fraction is preferably first dissolved in a physiological (0.9%) sodium chloride solution to give an about 5% protein solution. Prior to the treatment with β-propiolactone, this protein solution should preferably be freed of lipids by a treatment with colloidal silica gel. A treatment with crosslinked dextrans or cellulose having diethylaminoethyl groups, and preferably with the anion exchangers known as DEAE-Sephadex A-50 or DEAE cellulose, may also be carried out.

When Precipitate III, for example, from the Rivanol/ammonium sulfate fractionation is used as starting material, this precipitate may first be dissolved in water and dialyzed against a phosphate buffer solution of pH 6.2, and the euglobulin precipitate so obtained may then be dissolved in physiological saline solution. The treatment with β-propiolactone is then carried out at temperatures ranging from about 20° to 37° C. and pH values between about 7 and 8.5, and preferably about 8, for about 2 to 10 hours, and preferably about 4 to 6 hours, until a constant pH value is obtained.

After the treatment with β-propiolactone, the solution obtained is worked up in known manner, for example, sterile filtered. A treatment with activated carbon may first be carried out.

The favorable properties of the immunoglobulin solutions obtained by the process in accordance with the invention are demonstrated by the following tests.

(1) Anticomplementary activity

| Product | Complement consumption (ml complement [1:30]) per 1 ml sample |
|---|---|
| IgM concentrate before treatment with β-propiolactone | 7 |
| IgM concentrate after treatment with β-propiolactone (0.12 ml β-propiolactone per 100 ml) | Max. 0.3 |

The anticomplementary activity corresponds to the values for commercial intravenously compatible preparations of the IgG type.

(2) Effect of β-propiolactone modification on bacterial antibody activities

| | Antibody activities | | |
|---|---|---|---|
| | At start | After treatment with 0.12 ml β-propiolactone per 100 ml 5% solution | |
| Type of bacteria | Score* (Strength of reaction) | Score* (Strength of reaction) | % |
| E. coli | 36 | 38 | 105 |
| Klebsiella | 37 | 26 | 70 |
| Pyocyaneus | 38 | 37 | 97 |
| Streptococcus viridans | 46 | 34 | 74 |
| Streptococcus haemolyticus | 40 | 30 | 75 |
| Enterococci | 28 | 24 | 86 |
| Staphylococci | 43 | 34 | 76 |

The antibody activity is largely preserved after the β-propiolactone treatment.

(3) Comparison of the antibody activities of a commercial intravenously administered immunoglobulin preparation with those of the preparation in accordance with the invention

| | Antibody activities (score values) against | | | | | | |
|---|---|---|---|---|---|---|---|
| Preparation | E. coli | Klebsiella | Pyo-cyaneus | Strept. virid. | Strept. haemol. | Entero-cocci | Staph' cocci |
| Commercial intravenous immunoglobulin** | 14 | 9 | 11 | 1 | 0 | 0 | 3 |
| Intravenous IgM concentrate in accordance with invention | 38 | 26 | 37 | 34 | 30 | 24 | 34 |

**Obtained by chemical modification with β-propiolactone.

(4) Comparison of the immunoglobulin composition of a commercial intravenously administered immunoglobulin preparation with that of an IgM concentrate in accordance with the invention

| Preparation | IgG | IgA (mg%) | IgM | Total protein content (%) | Anticomplementary activity (ml complement [1:30] per 1 ml) |
|---|---|---|---|---|---|
| Commercial intravenous immunoglobulin* | 4900 | 100 | Traces | 5.0 | 0.3 |
| Intravenous IgM concentrate in accordance with invention | 4000 | 500 | 500 | 5.0 | 0.3 |

*Obtained by chemical modification with β-propiolactone.

The examples which follow will serve to illustrate the invention.

EXAMPLE 1

Cohn fraction III of human plasma was dissolved in 0.9% saline solution to give a 5% protein solution, freed of lipids with 3% Aerosil, and treated with 80 mg DEAE-Sephadex A-50 per gram of protein. The solution, which had a protein concentration of 5%, was then treated at pH 8.0 and 37° C. with 0.1 ml β-propiolactone per 100 ml of solution until a constant pH value was obtained. The solution obtained was dialyzed in known manner against 0.9% saline solution and sterile filtered. It was then suited for intravenous administration.

EXAMPLE 2

Cohn fraction III of human plasma heated for 2 hours to 56° C. was dissolved in 0.9% saline solution to give a 5% protein solution, freed of lipids with 3% Aerosil, and treated with 80 mg DEAE-Sephadex A-50 per gram of protein. The solution, whose protein concentration was 5%, was then treated at pH 8.0 and 37° C. with 0.05 ml β-propiolactone per 100 ml of solution until a constant pH value was obtained. The solution obtained was worked up in known manner by means of dialysis and sterile filtration and was then suited for intravenous administration.

EXAMPLE 3

Cohn fraction III of human plasma was dissolved in 0.9% saline solution to give a 5% solution, freed of lipids with 3% Aerosil, and treated with 80 mg DEAE-Sephadex A-50 per gram of protein. The solution was then diluted with 0.05 molar acetate buffer to 1.5% protein, adjusted to a pH of 4.8, and treated with 1.5 ml octanoic acid per 100 ml of solution and with 0.4 g $Ca_3(PO_4)_2$ per 100 ml of solution. After centrifugation and dialysis against 0.9% saline solution, the supernatant was weakly concentrated and at a protein concentration of 5% treated at pH 8.0 and room temperature (20° to 25° C.) with 0.12 ml β-propiolactone per 100 ml of solution until a constant pH value was obtained. After treatment with charcoal, the solution was sterile filtered and was then suited for intravenous administration.

EXAMPLE 4

Precipitate III from a Rivanol/ammonium sulfate fractionation was dissolved in water to give a solution having a protein concentration of 3%. An euglobulin precipitation was then carried out by dialysis against 0.0005 molar phosphate buffer of pH 6.2. After the precipitate had been dissolved in 0.9% saline solution to give a 5% protein solution, the latter was treated with 0.15 ml β-propiolactone per 100 ml of solution at pH 8.0 and 37° C. until a constant pH value was obtained. Then it was sterile filtered. The solution obtained was suitable for intravenous administration.

It will be appreciated that the instant specification and examples are set forth by way of illustration and not limitation, and that various modifications and changes may be made without departing from the spirit and scope of the present invention.

What is claimed is:

1. A process for the preparation of an immunoglobulin solution containing IgM in concentrated form and suited for intravenous administration, comprising treating an IgM-containing protein fraction obtained by conventional fractionation from blood plasma or serum with β-propiolactone in an amount such that the ratio of β-propiolactone to a 5% solution of the IgM-containing proteins is from about 0.05 to 0.15 ml per 100 ml.

2. A process according to claim 1, wherein the treatment with β-propiolactone is carried out for about 2 to 10 hours at a temperature ranging from about 20° to 37° C. and a pH between about 7 and 8.5.

3. A process according to claim 1, wherein the starting material used is a Cohn fraction III of human blood plasma which has been dissolved in physiological saline solution to a concentration of about 5% protein.

4. A process according to claim 1, wherein prior to the treatment with β-propiolactone the IgM-containing protein fraction is freed of lipids by treatment with colloidal silica gel and with crosslinked dextrans or diethylaminoethyl cellulose.

5. A process according to claim 1, wherein the treatment with β-propiolactone is carried out until a substantially constant pH value is obtained and the solution obtained is thereafter sterile filtered.

6. A process according to claim 4, wherein the starting material used is a Cohn fraction III of human blood plasma which has been dissolved in physiological saline solution to a concentration of about 5% protein, the treatment with β-propiolactone is carried out at about 20° to 37° C. for about 4 to 6 hours until a substantially constant pH of about 8 is obtained, and the solution is thereafter sterile filtered.

7. An intravenously injectable IgM-containing solution produced by the process of claim 1, having a maximum complement consumption per ml at a 30-fold dilution of 0.3, exhibiting at least about 70% of the antibody activity of the initial protein fraction against E. coli, Klebsiella, Pyocyaneus, *Streptococcus viridans, Streptococcus haemolyticus,* Enterococci and Staphylococci and having an IgM content of about 10% based on total globulins.

8. An intravenously injectable IgM-containing solution produced by the process of claim 6, having a maximum complement consumption per ml at a 30-fold dilution of 0.3, exhibiting at least about 70% of the antibody activity of the initial protein fraction against E. coli, Klebsiella, Pyocyaneus, *Streptococcus viridans, Streptococcus haemolyticus,* Enterococci and Staphylococci and having an IgM content of about 10% based on total globulins.

9. In the intravenous administration of IgM, the improvement which comprises employing an IgM-containing solution according to claim 7.

10. In the intravenous administration of IgM, the improvement which comprises employing an IgM-containing solution according to claim 8.

* * * * *

UNITED STATES PATENT AND TRADEMARK OFFICE
CERTIFICATE OF CORRECTION

PATENT NO. : 4,318,902
DATED : Mar. 9, 1982
INVENTOR(S) : Wolfgang Stephan

It is certified that error appears in the above—identified patent and that said Letters Patent is hereby corrected as shown below:

Column 3, before line 20, Insert --*) The "score" represents the sum of the agglutination strengths of the individual steps of a geometric dilution series:
++++ = 10    + = 3
+++ = 8      ± = 1
++ = 5
--.

Signed and Sealed this

Seventeenth Day of August 1982

[SEAL]

Attest:

Attesting Officer

GERALD J. MOSSINGHOFF

Commissioner of Patents and Trademarks